United States Patent [19]

Yoshimura et al.

[11] 4,334,117
[45] Jun. 8, 1982

[54] PROCESS FOR PRODUCING ALKADIENES

[75] Inventors: Noriaki Yoshimura; Masuhiko Tamura, both of Kurashiki, Japan

[73] Assignee: Kuraray Co., Ltd., Kurashiki, Japan

[21] Appl. No.: 183,500

[22] Filed: Sep. 4, 1980

[30] Foreign Application Priority Data

Sep. 10, 1979 [JP] Japan .................................. 54-116276

[51] Int. Cl.³ ............................................. C07C 11/12
[52] U.S. Cl. ................................... 585/509; 585/511; 585/514
[58] Field of Search ........................ 585/509, 511, 514

[56] References Cited

U.S. PATENT DOCUMENTS

| | | | |
|---|---|---|---|
| 3,732,328 | 5/1973 | Wright | 585/509 |
| 3,823,199 | 7/1974 | Wright | 585/509 |
| 4,020,121 | 4/1977 | Kister et al. | 585/511 |
| 4,180,694 | 12/1979 | Nozaki | 585/511 |
| 4,229,605 | 10/1980 | Nozaki | 585/511 |
| 4,229,606 | 10/1980 | Nozaki | 585/509 |
| 4,243,829 | 1/1981 | Pittman | 585/511 |

*Primary Examiner*—Delbert E. Gantz
*Assistant Examiner*—Joseph A. Boska
*Attorney, Agent, or Firm*—Barry Kramer

[57] ABSTRACT

This invention provides an improved process for producing alkadienes which comprises (1) contacting butadiene or isoprene with a catalyst such as platinum or palladium or a compound of one of said metals in a sulfolane solution, in the presence of a tertiary lower alkylamine formate and at least one phosphine compound of the formula:

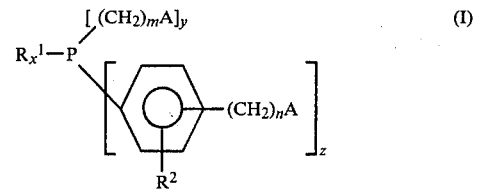

wherein $R^1$ is a substituted or unsubstituted $C_{1-10}$ hydrocarbon group; $R^2$ is H, a saturated aliphatic $C_{1-5}$ hydrocarbon group, nitro or halogen; m is 1, 2 or 3; n is 0 or 1; x is 0, 1 or 2; y and z each is 0, 1, 2 or 3 (provided that y and z are not zero concurrently and $x+y+z=3$); A is $-SO_3M$ wherein M is a cation selected from among H, alkali metals, alkaline earth metals and $NH_4$ or the formate or an inorganic acid salt of

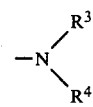

wherein $R^3$ and $R^4$ each means a saturated aliphatic $C_{1-4}$ hydrocarbon group in an amount of 4 to 200 moles per gram atom of the metal constituting the catalyst to form dimeric alkadienes; (2) separating the reaction mixture into an alkadiene-containing layer and a catalyst-containing layer; and (3) recycling the catalyst-containing layer to the alkadiene production process. The improved process makes it possible to maintain the catalytic activity over a prolonged period of time and to facilitate separation and reuse of the catalyst.

7 Claims, No Drawings

PROCESS FOR PRODUCING ALKADIENES

BACKGROUND OF THE INVENTION

1. Field of the Invention

This invention relates to a process for producing alkadienes by dimerization of butadiene or isoprene.

2. Description of the Prior Art

It is known that contacting an acyclic conjugated diolefin such as butadiene with a catalyst such as platinum, a platinum compound, palladium, a palladium compound or the like in the presence of a reducing agent in either a polar solvent or a nonpolar solvent yields the corresponding 1,6- and 1,7-octadiene (U.S. Pat. Nos. 3,732,328 and 3,823,199). U.S. Pat. No. 3,732,328 states that such a trisubstituted phosphine as triphenyl phosphine, as well as copper salts, are useful for enhancing the catalyst activity and for prolonging the catalyst life if the dimerization reaction is carried out in a steel reaction vessel. It is also known that the addition of an excess amount of the phosphine in the reaction system for telomerizing butadiene leads to a decrease in reaction rate (J. Organometallic Chemistry 49 473 (1973) and ibid. 137 309 (1977)). For this reason, in the examples of U.S. Pat. No. 3,732,328, the phosphine is used in an amount of at most 2 moles per gram atom of platinum or palladium.

When phosphine is not used in excess, however, the platinum or palladium metal complex in solution is extremely unstable against heat, which leads to a decrease in catalytic activity due to thermal decomposition of the metal complex and deposition of metallic platinum or palladium on the wall of the distillation vessel when the reaction mixture is subjected directly to distillation. Accordingly, for the purpose of stabilizing the catalyst against heat in the known processes, it is necessary to use the phosphine in excess amounts at the sacrifice of catalytic activity. Further, in cases wherein distillation is employed to separate the desired reaction product from the reaction mixture containing the catalyst, high-boiling by-products accumulate in the reaction system as the catalyst is reused, and as a result the catalytic activity is decreased.

For the commercial production of alkadienes by the dimerization of acyclic conjugated diolefins, it is particularly important to maintain the catalytic activity and to separate the catalyst from the reaction mixture in such manner that the catalyst does not decompose nor decrease its activity and can easily be reused in the dimerization reaction.

It has now been found that the above problems can be solved efficiently in accordance with the present invention in a very simple manner by (1) contacting butadiene or isoprene with at least one catalyst selected from the group consisting of platinum and palladium and compounds of said metals in a sulfolane solution, in the presence of a tertiary lower alkylamine formate and at least one phosphine compound of the general formula (I)

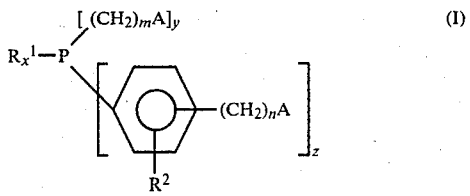

wherein $R^1$ is a substituted or unsubstituted hydrocarbon group of 1 to 10 carbon atoms; $R^2$ is a hydrogen atom, a saturated aliphatic hydrocarbon group of 1 to 5 carbon atoms, a nitro group or a halogen atom; m is equal to 1, 2 or 3; n is equal to 0 or 1; x is equal to 0, 1 or 2; y and z each is 0, 1, 2 or 3 (provided that y and z are not concurrently equal to 0 and that $x+y+z=3$); A is $-SO_3M$ wherein M is a cation selected from the group consisting of H, alkali metals, alkaline earth metals and $NH_4$ or the formate or an inorganic acid salt of

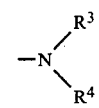

wherein $R^3$ and $R^4$ each is a saturated aliphatic hydrocarbon group of 1 to 4 carbon atoms, in an amount of 4 to 200 moles per gram atom of the metal constituting the catalyst to form dimeric alkadienes; (2) separating the reaction mixture into an alkadiene-containing layer and a catalyst-containing layer; and (3) recycling said catalyst-containing layer to the alkadiene production process.

The essential features of this invention reside in conducting the dimerization reaction in a sulfolane solution and in the use of both a tertiary lower alkylamine formate and at least one phosphine compound of the general formula (I) in an amount of 4 to 200 moles per gram atom of the metal as the catalyst. By virtue of these features, the catalytic activity can be maintained over a prolonged period of time in spite of using the phosphine compound in excess. The catalyst and the reaction product can be easily separated from the reaction mixture and the catalyst so separated, exhibits almost the same catalytic activity as in the preceding run of the reaction. Moreover, in accordance with this invention, the dissolution of the catalyst into the product during the separation of the catalyst from the reaction mixture is almost negligible and since the loss of the catalyst is thus minimized, butadiene or isoprene can be dimerized into alkadiene advantageously on a commercial scale.

The solvent to be employed in the process of this invention must not react readily with the starting material butadiene or isoprene and must be capable of separating the reaction mixture into an alkadiene-containing layer and a solvent layer containing the catalyst. In addition, the solvent must be chemically stable. When solvents such as ethylene glycol, diethylene glycol, nitromethane or the like, are employed in place of sulfolane in the process of this invention, the catalyst can be separated from the reaction mixture. Such solvents, however, are not satisfactory from a commercial viewpoint because the solvents react easily with butadiene or isoprene. When solvents such as acetone, tetrahydrofuran, dimethylformamide, ethyl acetate, t-butanol or the like, are employed in place of sulfolane, the product alkadiene is readily miscible with the solvent to form a homogeneous layer and, therefore the use of phosphine compounds of general formula (I) does not result in catalyst separation from the reaction mixture. If, in the process of this invention, a triarylphosphine such as triphenylphosphine, tri-n-butylphosphine, etc. or a trialkylphosphine is employed in place of a phosphine compound of the above-mentioned general formula (I), the catalyst dissolves into the product, i.e., dimeric alkadiene, so that the above-mentioned advantages in connection with the separation of the catalyst would not be realized.

DETAILED DESCRIPTION OF THE INVENTION

The phosphine compound employed according to this invention must not be soluble in alkadienes but be soluble in sulfolane solution. In the phosphine compounds of general formula (I) which satisfy the above requirements, $R^1$ is a substituted or unsubstituted hydrocarbon group of 1 to 10 carbon atoms. The hydrocarbon group is exemplified by saturated aliphatic hydrocarbon groups (e.g. methyl, ethyl, propyl, butyl, octyl); alicyclic hydrocarbon groups (e.g. cyclohexyl, cyclopentyl); alkenyl groups (e.g. decenyl, hexenyl, cyclohexenyl) and aromatic hydrocarbon groups (e.g. phenyl, benzyl, phenylbutenyl, tolyl, xylyl, p-ethylphenyl, p-methoxyphenyl, p-chlorophenyl). The term "substituted hydrocarbon group" is intended to include those groups substituted by substituent groups or atoms inert to the reaction, such as lower alkyl, lower alkoxy and halogen. Referring to the general formula (I), $R^2$ is a hydrogen atom, a saturated aliphatic hydrocarbon group of 1 to 5 carbon atoms (e.g. methyl, ethyl, propyl, isopropyl, butyl, pentyl, isopentyl), a nitro group or a halogen atom. Preferred examples of M in general formula (I) are H, Na, K, Ca and $NH_4$, and the phosphines in which A represents $—SO_3M$ are exemplified by the following compounds: $(C_4H_9)_2PCH_2SO_3H$, $(C_4H_9)_2PCH_2CH_2SO_3H$, $(C_8H_{17})_2PCH_2CH_2SO_3H$, $CH_3(C_6H_5)PCH_2CH_2SO_3H$, $(C_6H_5)_2PCH_2CH_2SO_3H$, $(C_6H_5)_2PCH_2CH_2CH_2SO_3H$, $C_6H_5P(CH_2CH_2SO_3H)_2$, $(C_6H_{13})_2PCH_2CH_2SO_3H$, $(o—CH_3C_6H_4)_2PCH_2CH_2SO_3H—$

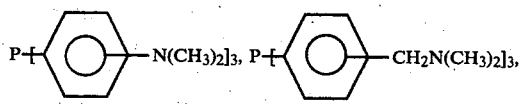

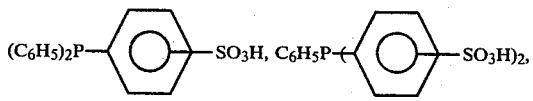

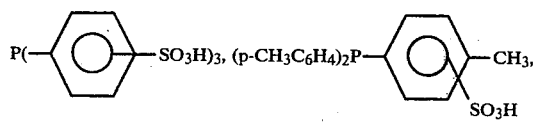

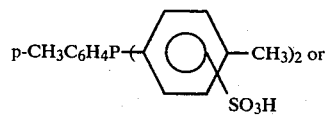

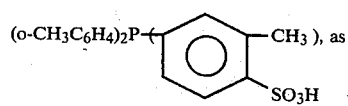

well as the sodium, potassium, calcium and ammonium salts of those compounds.

Of these compounds, those which are preferred from the standpoint of ease of production are

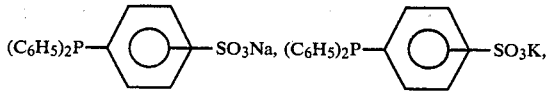

$(C_6H_5)_2PCH_2CH_2SO_3Na$ and $(C_6H_5)_2PCH_2CH_2SO_3K$.

Referring, further, to general formula (I), $R^3$ and $R^4$, respectively, mean a saturated aliphatic hydrocarbon group of 1 to 4 carbon atoms, e.g. methyl, ethyl, propyl, isopropyl, butyl, and the phosphine in which A is the formate or an inorganic acid salt of

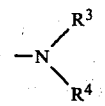

is exemplified by the following compounds. The formates and inorganic acid salts of $P[CH_2N(C_2H_5)_2]_3$, $(C_4H_9)_2PCH_2N(CH_3)_2$, $(C_4H_9)_2PCH_2CH_2N(CH_3)_2$, $P[CH_2CH_2CH_2N(CH_3)_2]_3$, $P[CH_2CH_2CH_2N(C_2H_5)_2]_3$, $P[CH_2CH_2N(t—C_4H_9)_2]_3$, $(C_8H_{17})P[CH_2N(CH_3)_2]_2$, $(C_6H_{13})_2PCH_2CH_2CH_2N(CH_3)_2$, $(C_6H_5)_2PCH_2N(CH_3)_2$, $(C_6H_5)_2PCH_2CH_2N(CH_3)_2$, $P[CH_2CH_2C_6H_4N(CH_3)_2]_3$,

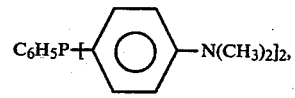

$C_6H_5P[CH_2N(CH_3)_2]_2$,

$C_6H_5P[CH_2CH_2CH_2N(CH_3)_2]_2$, and

The inorganic acids forming said inorganic acid salts may be any acid salts that are able to react with the amines to form salts and can thus be selected from among such acids as $H_3BO_3$, $NaH_2BO_3$, $H_3PO_4$, $NaH_2PO_4$, $KH_2PO_4$, $Na_2HPO_4$, $K_2HPO_4$, $NaHSO_4$ and $HCl$. These phosphine compounds may be used alone or as a mixture of two or more thereof.

When the phosphine compound of general formula (I) is a phosphine compound containing an amino group, it is added in the form of a formate salt or inorganic acid salt, although such salt may be produced in the reaction system by adding the amino containing phosphine compound of general formula (I) and either formic acid or an inorganic acid independently to the reaction system. The production ratio of 1,6-alkadiene to 1,7-alkadiene can be varied by varying the species of such salt. The phosphine compound is used in a ratio of 4 to 200 moles, preferably 6 to 50 moles, to each gram atom of the metal constituting the catalyst. By adding the phosphine compound of general formula (I) with the afore-mentioned ratio, the catalytic activity is effectively maintained over a prolonged period of time.

The reaction according to this invention is carried out in a sulfolane solution. As a result, the reaction mixture is effectively separated into a layer containing the alkadiene and a sulfolane layer containing the catalyst. The amount of the sulfolane is preferably about 1/10 to about 100 times the volume of the butadiene or isoprene.

In accordance with this invention, the dimerization reaction of butadiene or isoprene is carried out while the amount of water contained in the reaction mixture is held at below 5 weight % and preferably at a level not over 2 weight %. If the water content is over 5 weight percent, both the selectivity of the reaction and the yield of octadiene are reduced.

The catalyst for use in the practice of this invention comprises one or more members of the group consisting of platinum and palladium and compounds of said respective metals. When any of the metals are employed as said catalyst, the metal can be used in supported form on a catalyst support inert to the reaction, carbon black being a typical example. In this case, at least a portion of the metal dissolves in the liquid phase with the progress of the reaction. The above-mentioned metals and metal compounds are not restricted by their species or valences. As examples of platinum compounds, there may be mentioned bis(1,5-cyclooctadiene)platinum, platinum acetate, platinum (II) chloride, platinum (IV) chloride, platinum (II) potassium chloride, platinum (IV) potassium chloride, platinum acetylacetonate. Palladium compounds include, for example, bis(1,5-cyclooctadiene)palladium, bis-π-allylpalladium, palladium acetate, palladium carbonate, palladium chloride, palladium citrate, palladium nitrate, palladium sulfate, palladium acetylacetonate, bis(benzonitrile)palladium chloride, sodium tetrachloropalladium, etc. Aside from these, it is also possible to employ conventional palladium complexes or palladium compounds. Higher valent transition metal compounds can be used as catalysts after treating them with a suitable reducing agent in the presence of a phosphine compound of general formula (I) so that such compounds will be made lower valence species. The reducing agent used for this purpose includes sodium borohydride, zinc dust, magnesium, hydrazine, etc. The reducing agent is advantageously used in an approximately stoichiometric amount for change of the valences of transition metal compounds. Among the metals and metal compounds mentioned hereinbefore, palladium and palladium compounds are particularly desirable in terms of catalyst activity and reaction selectivity. The concentration of the catalyst in the reaction system is $1 \times 10^{-6}$ to 1 gram atom, preferably $1 \times 10^{-5}$ to $1 \times 10^{-2}$ gram atom, as the metal per liter of the reaction mixture.

The tertiary lower alkylamine formate to which the present invention is applicable includes trimethylamine formate, triethylamine formate, tripropylamine formate, triisopropylamine formate, tributylamine formate, triisobutylamine formate, etc. Among the above-mentioned formates, triethylamine formate is particularly preferred from the view point of catalyst separation, catalytic activity and availability. The use of the tertiary lower alkylamine formate leads to increases in reaction rate and reaction selectivity. The preferred amount of the tertiary lower alkylamine formate based on the starting material butadiene or isoprene is 0.01 to 5 molar equivalents and, for still better results, 0.1 to 2 molar equivalents. As to the manner of addition of the tertiary lower alkylamine formate, there can be used a method which comprises adding a tertiary lower alkylamine and formic acid independently to the reaction system so that the tertiary lower alkylamine formate may be produced therein.

Butadiene need not necessarily be of high purity but, for example, a butane-butene distillate fraction containing butadiene can be directly used as a starting material for the reaction according to this invention.

The dimerization reaction of butadiene or isoprene is performed by feeding the butadiene or isoprene into a sulfolane solution containing the catalyst component and tertiary lower alkylamine formate in an inert gas ($N_2$ or $CO_2$) atmosphere and stirring the reaction mixture. The reaction temperature is below 200° C. and is usually selected from the range of 20° C. to 120° C. The reaction can be carried out batchwise or continuously. As far as the latter is concerned, the reaction is carried out by adding formic acid to the reaction system continuously, removing the formed carbon dioxide from the reaction system continuously or intermittently and maintaining the molar ratio of formic acid to the total amount of formate salt contained in the reaction system being $\leqq 1$.

In the method according to the present invention, at least a portion of the reaction mixture is separated into phases. Thus, when the reaction mixture is cooled to ambient temperature and allowed to stand, the reaction mixture is separated into a layer containing the product alkadiene and a sulfolane layer containing the catalyst. If, in this operation, a saturated aliphatic hydrocarbon containing 4 to 16 carbon atoms is allowed to be present in an appropriate proportion, the alkadiene can be advantageously separated from the reaction mixture. As examples of such saturated aliphatic hydrocarbon there may be mentioned butane, pentane, hexane, heptane, isooctane, petroleum ether and kerosene. While the amount of saturated aliphatic hydrocarbon is not particularly critical, the range of about 1/10 to about 10 times the volume of starting butadiene or isoprene is desirable. It is also feasible to add the saturated aliphatic hydrocarbon in an amount of about 1/10 to about 5 times in volume based on that of butadiene or isoprene at the start of the reaction. The entire amount of a portion of the sulfolane layer containing the catalyst, either as is or after being subjected to a regeneration process if necessary, is recycled to the process for the dimerization of the butadiene or isoprene. Recovery of alkadiene from said alkadiene-containing layer can be effected by the per se conventional separatory procedures but, generally, distillation is a practically preferred procedure. The alkadiene need not necessarily be isolated but said alkadiene-containing layer may be directly utilized, for example, as a starting material for a hydroformylation reaction.

By the process according to the present invention there can be obtained 1,6- and 1,7-octadienes. 1,7-Octadiene, in particular, is a valuable intermediate for the synthesis sebacic acid, $C_{10}$ diol and $C_{10}$ diamine and is also useful as a crosslinking agent in the polymerization of olefins. Moreover, isoprene yields dimethyloctadienes which are important intermediates for the production of perfumes such as linalool, citronellol, etc.

The phosphine compounds used in the following Examples and Comparative Examples were synthesized by the procedures described in the literature.

The Examples are intended to further illustrate the present invention and should by no means be construed as limiting the scope of the invention.

EXAMPLE 1

A 300-ml autoclave equipped with a butadiene inlet, an octadiene outlet and a magnetic stirrer was charged, under nitrogen gas atmosphere, with 28 mg of palladium acetate, 300 mg of sodium diphenylphosphinobenzene-m-sulfonate dihydrate [prepared by the method described in J. Chem. Soc., 278 (1958)], 50 ml of sulfolane substantially purged of dissolved oxygen by passing nitrogen, 26 g of formic acid, 57 g of triethylamine and 10 ml of 1-octene (as internal standard) and then was cooled and further charged with 65 g of butadiene. The autoclave contents were stirred at 70° C. for 3 hours (the reaction pressure being 13 kg/cm$^2$), and then cooled to room temperature. After recovering the unreacted butadiene, the liquid reaction mixture was transferred to a separatory funnel. Two layers formed, and the upper layer was colorless. A sample from the upper layer was analyzed by gas chromatography, and it was found that the yield of octadienes was 99% based on the reacted butadiene (the conversion being 94% based on the charged butadiene) and that the octadienes consisted of 86% of 1,7-octadiene and 14% of 1,6-octadiene. Formic acid (26 g) was added to the reaction mixture with cooling, and the upper layer was separated. The upper layer, weighing 62 grams, was distilled under reduced pressure (100 mmHg) to give 61 g of an octadiene fraction boiling at 65° C. The upper layer contained dissolved palladium at a level of 0.8 ppm and phosphorus at 0.1 ppm.

EXAMPLE 2

The procedure of Example 1 was followed using the same reaction apparatus as in Example 1. After completion of the reaction, the autoclave was cooled to room temperature, then depressurized, and further cooled to 0° C. Formic acid (26 g) was added, and the mixture was stirred gently and then allowed to stand. The upper layer (55 g) was taken out. The reaction apparatus containing the remaining liquid was cooled on a dry ice-acetone bath, 65 g of butadiene and 10 ml of 1-octene were introduced into the apparatus, and the reaction was again conducted at 70° C. for 3 hours. After completion of the reaction, the upper layer (62 g) was removed. Gas chromatographic analysis of the upper layer revealed that the rate of conversion of butadiene was 94% and the octadiene yield was 99% based on the butadiene converted, with 86% of 1,7-octadiene and 14% of 1,6-octadiene. The above procedure was repeated four times and substantially the same results as above were obtained.

COMPARATIVE EXAMPLES 1-2

The same apparatus as in Example 1 was charged, under nitrogen atmosphere, with 144 mg tetrakis(triphenylphosphine)palladium, 50 ml of tetrahydrofuran, 26 g of formic acid, 59 g of triethylamine and 10 ml of 1-octene. After closing the autoclave, 65 g of butadiene was charged. The autoclave contents were stirred at 65° C. for 3 hours, and then cooled to room temperature. The unreacted butadiene was recovered. Then, the reaction mixture was transferred to the distillation apparatus under nitrogen atmosphere. A part of the reaction mixture analyzed by gas chromatography, and it was found that the yield of octadienes was 98% based on the butadiene converted (the conversion being 92% based on the charged butadiene), and that the octadienes consisted of 86% of 1,7-octadiene and 14% of 1,6-octadiene. The reaction mixture was distilled for 3 hours under reduced pressure of 200 mmHg. Octadienes were obtained at the boiling point of 75°–77° C. About 10 ml of octadienes containing catalyst remained and were transferred into the autoclave described above with 50 ml tetrahydrofuran, 26 g of formic acid, 59 g of triethylamine and 10 ml of 1-octene. After 65 g of butadiene was charged, the first reaction was repeated. The above procedure was repeated four times. Palladium metal was deposited on the distillation flask on the third time and catalytic activity decreased abruptly as a result. The same experiment described above was carried out, except tetrahydrofuran was changed to dimethylformamide. Table 1 shows the replicate results.

TABLE 1

| Comparative Example | Solvent | Run | Butadiene Conversion (%) | Selectivity (%) for 1,7-Octadiene | Selectivity (%) for 1,6-Octadiene |
|---|---|---|---|---|---|
| 1 | Tetrahydrofuran | 1 | 92 | 84 | 14 |
|  |  | 2 | 92 | 85 | 13 |
|  |  | 3 | 83 | 87 | 11 |
|  |  | 4 | 76 | 87 | 11 |
| 2 | Dimethylformamide | 1 | 93 | 87 | 11 |
|  |  | 2 | 86 | 87 | 11 |
|  |  | 3 | 63 | 88 | 10 |
|  |  | 4 | 41 | 88 | 10 |

EXAMPLE 3

The same apparatus as in Example 1 was charged, under nitrogen gas atmosphere, with 33 mg of palladium acetylacetonate, 274 mg of tris(p-dimethylaminophenyl)phosphine [prepared by the method described in J. Prakt. Chem. 33, 168 (1967)], 500 mg of stannous acetate, 50 ml of sulfolane, 26 g of formic acid, 57 g of triethylamine and 10 ml of 1-octene. After closing the autoclave, 65 g of butadiene was charged. The autoclave contents were stirred at 60° C. for 3 hours, and then cooled to room temperature. The unreacted butadiene was recovered. Then, 26 g of formic acid was added gradually with stirring and the reaction mixture was transferred to a separatory funnel. Two layers resulted. The upper layer was colorless. Analysis of the upper layer by gas chromatography showed that the octadiene yield was 99% based on the butadiene converted (95% based on the butadiene charged), with 89% of 1,7-octadiene and 11% of 1,6-octadiene. The upper layer contained dissolved palladium at a level of 1.0 ppm and phosphorus at 0.2 ppm.

EXAMPLE 4 AND COMPARATIVE EXAMPLES 3-6

A 20 ml glass pressure bottle was charged with 2.2 mg of palladium acetate, sodium diphenylphosphinobenzene-m-sulfonate dihydrate, 2.26 g of triethylamine, 1.03 g of formic acid, 6 ml of solvent and 5 ml of butadiene. The bottle was capped and the reaction was conducted in a shaker equipped with thermostat at 65° C. for 1 hour. A variety of solvents and amounts of organophosphine were used. After the reaction was carried out, the liquid reaction mixture was analyzed by gas chromatography. The results obtained are shown in Table 2.

40 g of aqueous sulfolane. After closing the autoclave, 11 g of butadiene were introduced into the autoclave

TABLE 2

| Example | Solvent | P/Pd molar ratio | Butadiene conversion (%) | Selectivity (%) for 1,7-Octadiene | Selectivity (%) for 1,6-Octadiene | Nature of reaction mixture |
|---|---|---|---|---|---|---|
| 4 | Sulfolane | 6 | 93 | 89 | 10 | Heterogeneous |
|  |  | 25 | 74 | 90 | 9 |  |
| Compar. 3 | Dimethylformamide | 6 | 93 | 89 | 10 | Homogeneous |
|  |  | 25 | 59 | 89 | 10 |  |
| Compar. 4 | 2,3-Butanediol | 6 | 87 | 78 | 21 | Homogeneous |
|  |  | 25 | 44 | 81 | 18 |  |
| Compar. 5 | Acetone | 6 | 91 | 79 | 20 | Homogeneous |
|  |  | 25 | 60 | 81 | 18 |  |
| Compar.[1] 6 | Ethylene glycol | 6 | 63 | 60 | 27 | Heterogeneous |

[1] In comparative Example 6, there were obtained as a by-product ethylene glycol mono-2,7-octadienyl ether (12%).

EXAMPLES 5-10

A 80-ml glass pressure bottle was charged with 0.1 mmole of palladium acetate, 0.4 mmole of an organophosphorus compound, 56 mmoles of triethylamine, 58 mmoles of formic acid, 10 ml of sulfolane and 10 ml of butadiene. The bottle was capped and the reaction was conducted in a shaker equipped with a thermostat at 70° C. for 3 hours. A variety of organophosphorus compounds were used. The liquid reaction mixture was cooled, 58 mmoles of formic acid and an internal standard compound were added, and gas chromatographic analyses were performed.

Table 3 shows the results obtained by varying the organophosphorus compound.

under pressure of carbon dioxide gas. Then, the reaction was carried out with stirring at 80° C. (internal temperature) for 2 hours, the autoclave was then cooled, and the liquid reaction mixture was taken out. The reaction mixture was analyzed by gas chromatography. The results are shown in Table 4.

TABLE 3

Octadiene synthesis with various organophosphorus compounds[1]

| Example | Organophosphorus compound | Butadiene conversion (%) | Selectivity (%) for 1,7-Octadiene | Selectivity (%) for 1,6-Octadiene |
|---|---|---|---|---|
| 5 | $P{+}(C_6H_4){-}CH_2N(CH_3)_2)_3$ | 95 | 85 | 14 |
| 6 | $P{+}(C_6H_4){-}N(CH_3)_2)_3 \cdot H_3BO_4$ | 92 | 89 | 10 |
| 7 | $Ph_2PCH_2N(CH_3)_2 \cdot H_3BO_4$ | 80 | 71 | 28 |
| 8 | $P{+}(C_6H_4){-}N(CH_3)_2)_3 \cdot NaH_2PO_4$ | 72 | 71 | 28 |
| 9 | $P{+}(C_6H_4){-}N(CH_3)_2)_3 \cdot H_3BO_4$ | 90 | 76 | 23 |
| 10 | $P{+}(C_6H_4{-}SO_3N_2))_3$ | 60 | 81 | 17 |

[1] The organophosphorus compound used in Example 7 was prepared by the method described in Helv. Chim. Acta 48, 1034 (1965).

EXAMPLES 11-13 AND COMPARATIVE EXAMPLES 7-8

The water content in the reaction system was varied by using aqueous sulfolane with its water content varied. A 100-ml autoclave with a magnetic stirrer was charged, under carbon dioxide atmosphere, with 0.1 mmole of palladium acetate, 1.0 mmole of $(C_6H_5)_2PC_6H_4SO_3Na$ (meta isomer), 17 g (0.168 moles) of triethylamine, 7.8 g (0.170 mmole) of formic acid, and

TABLE 4

| Example | Amount of water in the reaction system (wt %) | Butadiene conversion (%) | Selectivity (%) for 1,7-Octadiene | Selectivity (%) for 1,6-Octadiene |
|---|---|---|---|---|
| 11 | 0.02 | 97 | 89 | 10 |
| 12 | 2.0 | 95 | 73 | 8 |
| 13 | 4.0 | 92 | 68 | 8 |
| Compar. 7 | 8.0 | 87 | 52 | 15 |
| Compar. 8 | 50.0 | 72 | 8 | 9 |

EXAMPLE 14

The same reaction vessel as in Example 5 was charged, under nitrogen gas atmosphere, with 0.65 mmole of bis-$\pi$-allylpalladium acetate, 6.5 mmoles of $Ph_2PC_6H_4SO_3Na$ (meta isomer), 11 g of triethylamine, 6 g of formic acid, 10 ml of sulfolane, 10 ml of isoprene, and 1 ml of 1,3,3,4-tetramethylpentane as an internal standard for gas chromatographic analysis. The reaction was carried out at a temperature of 50° C. for 24 hours. After completion of the reaction, the liquid reaction mixture formed two layers. Gas chromatographic analysis of the upper layer showed that the rate of conversion of isoprene was 39% and that the product consisted of 20% (based on the isoprene converted) of 3,6-dimethyl-1,7-octadiene, 68% of 3,7-dimethyl-1,7-octadiene, 3% of 3,7-dimethyl-1,6-octadiene and 9% of 2,7-dimethyl-1,7-octadiene.

What is claimed is:

1. A process for producing alkadienes which comprises (1) contacting butadiene or isoprene with at least one catalyst selected from the group consisting of platinum and palladium and compounds of said metals in a sulfolane solution, in the presence of a tertiary lower alkylamine formate and at least one phosphine compound of the general formula (I)

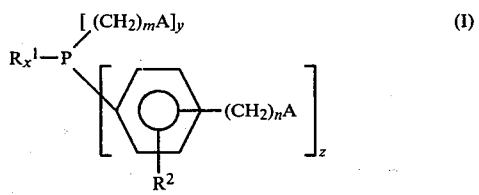  (I)

wherein $R^1$ is a substituted or unsubstituted hydrocarbon group of 1 to 10 carbon atoms; $R^2$ is a hydrogen atom, a saturated aliphatic hydrocarbon group of 1 to 5 carbon atoms, a nitro group or a halogen atom; m is equal to 1, 2 or 3; n is equal to 0 or 1; x is equal to 0, 1 or 2; y and z each is 0, 1, 2 or 3 (provided that y and z are not concurrently equal to 0 and that $x+y+z=3$); A is $-SO_3M$ wherein M is a cation selected from the group consisting of H, alkali metals, alkaline earth metals and $NH_4$ or the formate or an inorganic acid salt of

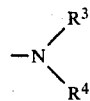

wherein $R^3$ and $R^4$ each is a saturated aliphatic hydrocarbon group of 1 to 4 carbon atoms, in an amount of 4 to 200 moles per gram atom of the metal constituting the catalyst to form dimeric alkadienes; (2) separating the reaction mixture into an alkadiene-containing layer and a catalyst-containing layer; and (3) recycling said catalyst-containing layer to the alkadiene production process.

2. A process as claimed in claim 1 wherein the reaction mixture is separated into an alkadiene-containing layer and a catalyst-containing layer in the presence of a saturated aliphatic hydrocarbon extractant.

3. A process as claimed in claim 1 wherein said catalyst is palladium or a compound of palladium and the concentration of said catalyst in the reaction system is $1\times 10^{-6}$ to 1 gram as the metal per liter of the reaction mixture.

4. A process as claimed in claim 1 wherein the tertiary lower alkylamine formate is a triethylamine formate.

5. A process as claimed in claim 1 wherein said phosphine compound of general formula (I) is used in a proportion of 6 to 50 moles per gram atom of the metal constituting said catalyst.

6. A process as claimed in claim 1 wherein said butadiene is a mixture containing butane and butene.

7. A process as claimed in claim 2 wherein said saturated aliphatic hydrocarbon is butane, pentane, hexane, heptane, isooctane, petroleum ether or kerosene.

* * * * *